United States Patent
Bob

(10) Patent No.: US 11,925,322 B2
(45) Date of Patent: Mar. 12, 2024

(54) ENDOSCOPE WITH EXTENSIBLE WORK CHANNEL

(71) Applicant: Konstantin Bob, Weinheim (DE)

(72) Inventor: Konstantin Bob, Weinheim (DE)

( * ) Notice: Subject to any disclaimer, the term of this patent is extended or adjusted under 35 U.S.C. 154(b) by 380 days.

(21) Appl. No.: 17/052,688

(22) PCT Filed: May 3, 2019

(86) PCT No.: PCT/EP2019/061421
§ 371 (c)(1),
(2) Date: Nov. 3, 2020

(87) PCT Pub. No.: WO2019/211457
PCT Pub. Date: Nov. 7, 2019

(65) Prior Publication Data
US 2021/0177247 A1    Jun. 17, 2021

(30) Foreign Application Priority Data
May 3, 2018   (DE) ..................... 10 2018 110 624.6

(51) Int. Cl.
*A61B 1/00*   (2006.01)
*A61B 1/005*  (2006.01)
(Continued)

(52) U.S. Cl.
CPC ............ *A61B 1/01* (2013.01); *A61B 1/00098* (2013.01); *A61B 1/0052* (2013.01); *A61B 1/0057* (2013.01); *A61B 1/018* (2013.01)

(58) Field of Classification Search
CPC ..... A61B 1/01; A61B 1/0008; A61B 1/00098; A61B 1/0051; A61B 1/0057; A61B 1/018;
(Continued)

(56) References Cited

U.S. PATENT DOCUMENTS

| | | | | |
|---|---|---|---|---|
| 4,245,624 A | * | 1/1981 | Komiya | A61B 1/12 604/95.04 |
| 5,343,853 A | * | 9/1994 | Komi | A61B 1/018 600/109 |

(Continued)

FOREIGN PATENT DOCUMENTS

| | | |
|---|---|---|
| DE | 2800362 A1 | 7/1978 |
| DE | 10143966 A1 | 3/2002 |

(Continued)

OTHER PUBLICATIONS

German Search Report for German Application No. 10 2018 110 624.6, with partial English translation, dated Nov. 21, 2018, 19 pages.

(Continued)

*Primary Examiner* — Timothy J Neal
*Assistant Examiner* — James Edward Boice
(74) *Attorney, Agent, or Firm* — RatnerPrestia

(57) ABSTRACT

A work channel arrangement of an endoscope for guiding medical tools and/or for the through-flow of media. The work channel arrangement has a work channel which is flexible at least in part and extensible relative to the endoscope and which can be moved from a first position, in which the work channel outlet is oriented in the axial direction of the endoscope head, to a second position in which it is extended in the distal direction relative to the first position and in which the work channel outlet is or can be deflected, by means of a guide mechanism, to a predetermined lateral or rearward direction.

8 Claims, 5 Drawing Sheets

(51) Int. Cl.
*A61B 1/01* (2006.01)
*A61B 1/018* (2006.01)

(58) Field of Classification Search
CPC ... A61B 1/00154; A61B 1/05; A61B 1/00101; A61B 17/3417; A61B 2017/00991; A61B 1/0052; A61B 1/00183
USPC ........................................................ 600/146
See application file for complete search history.

(56) References Cited

U.S. PATENT DOCUMENTS

| | | | |
|---|---|---|---|
| 6,083,170 A | | 7/2000 | Ben-Haim |
| 6,126,649 A | * | 10/2000 | VanTassel ......... A61M 25/0147 604/95.04 |
| 6,152,870 A | * | 11/2000 | Diener ................. A61B 1/0008 600/153 |
| 6,270,453 B1 | | 8/2001 | Sakai |
| 6,482,149 B1 | | 11/2002 | Torii |
| 6,641,528 B2 | | 11/2003 | Torii |
| 2001/0025174 A1 | | 9/2001 | Daniel et al. |
| 2002/0161284 A1 | * | 10/2002 | Tanaka .................... A61B 1/05 600/176 |
| 2005/0006009 A1 | * | 1/2005 | Esashi ............... A61M 25/0158 148/518 |
| 2005/0131279 A1 | * | 6/2005 | Boulais .............. A61B 1/00071 600/141 |
| 2005/0234296 A1 | * | 10/2005 | Saadat ................ A61B 1/0008 600/173 |
| 2007/0208219 A1 | * | 9/2007 | Carter .................... A61B 1/018 600/107 |
| 2009/0247821 A1 | * | 10/2009 | Rogers ............... A61B 1/00098 600/104 |
| 2010/0228086 A1 | | 9/2010 | Ohki et al. |
| 2013/0109916 A1 | * | 5/2013 | Levy .................. A61B 1/00177 600/109 |
| 2015/0238068 A1 | | 8/2015 | Rose et al. |
| 2018/0249894 A1 | | 9/2018 | Kolberg et al. |
| 2019/0059702 A1 | * | 2/2019 | Hosogoe ............ A61B 1/00101 |
| 2020/0100656 A1 | | 4/2020 | Bob |

FOREIGN PATENT DOCUMENTS

| | | |
|---|---|---|
| DE | 69732566 T2 | 1/2006 |
| DE | 102012220578 A1 | 5/2014 |
| DE | 102013222279 A1 | 5/2015 |
| DE | 102015113016 A1 | 2/2017 |
| DE | 102015113018 A1 | 2/2017 |
| DE | 102017107978 A1 | 10/2018 |

OTHER PUBLICATIONS

International Preliminary Report on Patentability for International Application No. PCT/EP2019/061421, dated Nov. 3, 2020, 7 pages.
International Search Report and Written Opinion for International Application PCT/EP2019/061421, dated Jul. 25, 2019, 9 pages.

\* cited by examiner

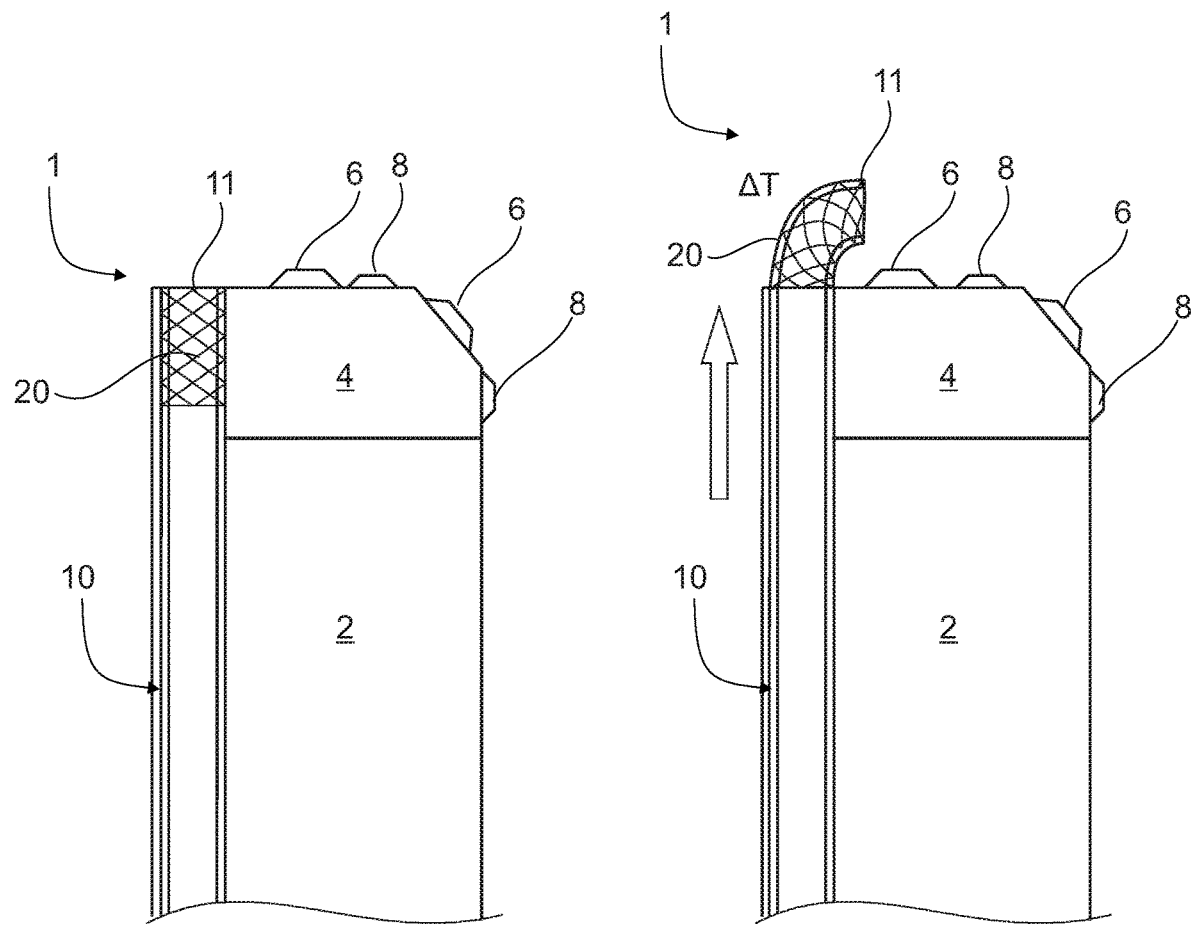
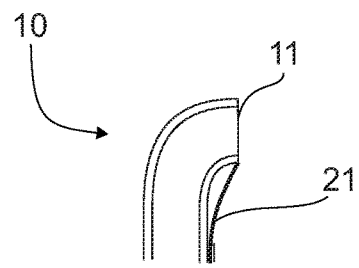
Fig. 4  Fig. 5
Fig. 5A

ENDOSCOPE WITH EXTENSIBLE WORK CHANNEL

This application is a U.S. National Phase application of PCT International Application No. PCT/EP2019/061421, filed May 3, 2019, which claims the benefit of DE 10 2018 110 624.6, filed May 3, 2018, both of which are incorporated by reference herein.

TECHNICAL FIELD

The present disclosure relates to a work channel arrangement of an endoscope as well as an endoscope and an (endoscope-separate) endoscope head attachment with such a work channel arrangement.

BACKGROUND OF THE INVENTION

Endoscopes are medical working tools used for the visual exploration of cavities in the body of a patient. They basically have optical devices at the distal endoscope end, i.e. the endoscope end facing the body (also known as endoscope head) and optionally a work channel which, starting from a proximal (not facing the body) endoscope portion or extracorporeal endoscope handle, extends through an (adjoining) flexible/bend-proof or rigid endoscope shaft to the endoscope head and enables the extracorporeal insertion and use of medical instruments such as forceps, scissors, needles, slings, knifes and the like.

Such endoscopes can optionally be provided with additional functions, e.g. by placing a cap or sleeve on the distal endoscope end/endoscope head radially on the outside of the endoscope head, which is provided or equipped with specific functions/functional elements, whereby the endoscope can not only be used for exploration and/or as access for therapeutic applications, but the endoscope itself can also be used as a minimally invasive instrument for performing a surgical procedure. Alternatively, it is provided to integrally equip special endoscopes for very specific medical applications with such functions, wherein such special designs are only suitable for this respective special application.

Various diagnostic and/or therapeutic procedures require, for example, imaging and/or, if necessary, therapeutic techniques on the biliary and/or pancreatic duct as well as on the hepatic ducts of the patient. Since the major duodenal papilla, which forms the common outlet of the biliary and pancreatic duct into the duodenum, protrudes laterally into the duodenum, conventional prograde endoscopes (facing in the longitudinal direction of the endoscope) are unsuitable for such procedures, since there is not enough pivoting space in the narrow duodenum (diameter 3 to 4 cm) to orientate their prograde optical unit and the work channel in a lateral-facing position, since a typical bending diameter of such devices is at about 12 cm.

PRIOR ART

From the prior art (e.g. US 2010/228086 A), duodenoscopes are known which are specially made for this purpose, which have a lateral (laterally facing) or retrograde (backward facing) optical unit (also called "side optics") as well as a laterally oriented work channel. At the exit of the work channel of such duodenoscopes, a so called Albarran lever is usually provided, which allows a targeted guidance/deflection of a tool guided in the work channel by pivoting. The laterally facing arrangement of the functional units on the endoscope head allows imaging and treatment in the duodenum area while optimally utilizing the available space.

However, such endoscopes with side optics are very complex and expensive to manufacture and have therefore been developed and manufactured so far as reusable devices. The curved work channel of such endoscopes as well as the complex construction with many undercuts of the Albarran lever have proven to be difficult to sterilize in practice or the sterilization process has turned out to be too material fatiguing for the sensitive devices, so that only disinfection is possible after a procedure with such a duodenoscope. As a result, a bacterial lawn (biofilm) may remain in the work channel and/or the auxiliary channel of the endoscope after a procedure. If this biofilm then peels off during a subsequent procedure, for example when an instrument is pushed through the work channel, it can, for example, enter the biliary duct and/or the pancreas duct and cause serious inflammation or even sepsis in the patient.

Furthermore, such devices have the disadvantage that they can only be used for very few, very specific procedures in the area of the duodenum, since neither the optical unit nor the work channel can be directed in the prograde direction. Moreover, navigation in the body with laterally facing endoscopes is generally rather difficult, since looking ahead always requires bending of the "deflecting portion" (actively bendable endoscope shaft-portion) directly upstream of the endoscope head by about 90°, which in turn requires more space in the lateral direction of the endoscope, which is only available in the stomach.

The distal deflecting portion of the shaft of a prograde flexible endoscope (looking straight ahead) with a bendable tip usually consists of articulated ring elements which form the supporting structure of the shaft and are operated and tilted against each other via Bowden cables, often called bending control cables. In order to facilitate insertion into the cavity and to prevent the intrusion of substances, the ring elements are surrounded by a flexible sheath made of a plastic material. In particular light and image guide cables, channels for fluids or endoscopic working instruments run inside the ring elements. The bending control cables are guided along the outside or inside of the ring elements. Such flexible endoscopes are disclosed, for example, in U.S. Pat. No. 6,270,453 B1, U.S. Pat. No. 6,482,149 B1 or DE 101 43 966 B4.

The smallest radius that the flexible or articulated portion of the shaft can assume is determined by the respective construction principle. For example, an articulated portion constructed with successive ring elements, each of which is articulated to the next, allows only a relatively large bending radius, since the individual ring elements each have only a small tilt angle to the next ring element. If the articulated connection of two elements only permits tilting about one axis, it is necessary for a spatial bending possibility to arrange elements with tilting axes alternately twisted against each other, so that only every second element can be deflected in a respectively desired direction; this further increases the possible minimum bending radius. The close range next to the shaft end is therefore not visible with an optical unit arranged in the tip of the endoscope.

As described, for example, in the prior art in DE 10 2013 222 279 A1 or DE 10 2012 220 578 A1, endoscopes with a pivoting optical unit separate from the rest of the endoscope head are furthermore known, which can look both in the prograde and in the lateral direction. However, such endoscopes do not have a work channel (i.e. they are used purely diagnostically) or they have a fixed work channel in the prograde direction and are therefore not suitable for the typically intended purposes of duodenoscopes which require a laterally-oriented work channel.

In summary, it can be said that the user is not able to perform minimally invasive interventions in the duodenum both in the prograde direction as well as in the lateral/retrospective close range of the endoscope with the endoscopes known to the prior art to date.

In view of the disadvantages of the prior art described above, the object of the present invention is to provide a work channel arrangement for an endoscope which enables an integrated, minimally invasive surgical treatment of the close range surrounding the endoscope tip (both lateral and prograde).

BRIEF DESCRIPTION OF THE INVENTION

The present invention basically relates to a work channel arrangement of an endoscope for guiding medical (minimally invasive) tools and/or for the flow of media. According to the invention, the work channel arrangement has a work channel which is designed to be flexurally elastic at least in sections (with its distal end portion) and extendable relative to the endoscope. At least this distal end portion of the work channel (or even the entire work channel) can be transferred or displaced/extended from a first axially retracted position to a second axially advanced position. In the first position, the distal work channel exit is oriented (orthograde) in the axial direction of the endoscope head. In the second position, which is extended distally in relation to the first position, the work channel exit can be deflected in a predetermined lateral or retrospective direction using the flexural elasticity of the distal end portion by means of a guiding device or it is compulsorily guided and deflected in the lateral direction by the guiding device during the extension movement. The work channel arrangement according to the invention thus allows an extension and simultaneous (or delayed) deflection of the distal work channel tip and thus enables treatment both in the orthograde and in the lateral direction of the endoscope head. In summary, the invention relates to a work channel arrangement with a work channel whose distal tip is designed in such a way that it can be extended and (for searching the major duodenal papilla) directed in a targeted manner.

According to a preferred embodiment, the work channel can be designed to be pulled from the first to the second position by means of an entrainer that can be operated from the handle and that is anchored to the work channel in the area of the work channel exit, e.g. by means of a control cable or Bowden cable. For this purpose, the entrainer is advantageously deflected by a deflection device (e.g. a deflection contour or cable control) positioned distally in front of the distal end of the work channel in the first position, so that the work channel is first pulled distally when a tensile force is applied from the proximal direction and then, following the deflection of the entrainer, is pulled into a lateral orientation relative to the longitudinal axis of the endoscope. A pulling force can either be applied manually from the operating side to the entrainer or the entrainer can be power-operated. A return spring or the like may be provided for retraction.

In accordance with a preferred embodiment, which may be claimed independently, the guiding device may have a convex guiding surface against which the work channel is pulled by the entrainer, whereby the guiding surface supports the work channel from radially inside and gives it a defined curvature. In other words, the work channel can nestle against the guide surface under the proximal tensile force of the entrainer and thus assume a predefined curved shape. Preferably, the guiding device can also deflect the entrainer. The guiding surface can especially preferably be trough-shaped or shaped as a groove, so that the work channel is supported and kept in track transversely to its pulling direction.

According to a preferred embodiment, which may be claimed independently, the working channel may have a telescopic and/or stretchable extension portion that extends in its axial direction when the working channel is subjected to a tensile load, thereby supporting the extension movement of a distal working channel portion. In this way, the extension of the working channel can be limited to a defined area, which reduces friction. In alternative embodiment, the entire work channel can be displaced relative to the rest of the endoscope during the extension movement or the length required for the extension movement is obtained from the elasticity/extensibility of the entire length of the work channel.

According to a preferred embodiment, which may be claimed independently, a distal endoscope head portion or a distal end cap of the endoscope head can be pivoted to a lateral position. In this case, the extendable work channel can be fixed to the distal endoscope head portion, so that when the endoscope head portion is pivoted, it pulls the work channel with it and the work channel extends. Since the work channel exit is fixed at an angle to the pivotable endoscope head portion, the work channel exit is also oriented laterally or retrospectively when the endoscope head portion is pivoted.

Advantageously, in such a embodiment, a guiding device can be folded open during a pivoting movement of the distal endoscope head portion, which supports the extended work channel from radially inside with a defined curved contour. This ensures that the work channel assumes a defined curvature that allows minimally invasive surgical instruments to be guided therein.

According to a preferred aspect of the invention, which may be claimed independently, the work channel may be located in a peripheral region of the cross-section of the endoscope. I.e. the work channel can either be guided inside or outside (along) the shaft and in the area of the outer circumference. The work channel arrangement should be adapted and designed in such a way that the distal end portion of the work channel is deflected in such a way that the work channel exit is oriented towards the edge region of the endoscope's cross-section opposite the work channel. In other words, the work channel can preferably be arranged in the edge region of the endoscope cross-section and, during extension, can be deflected such that it extends over the endoscope cross-section. In this way, the diameter of the curvature can be maximized when oriented in the lateral direction, which facilitates the passage of minimally invasive surgical instruments.

Especially preferably, the work channel can be arranged at the edge region facing away from the optical unit of an endoscope and, in the extended state, deflected by the guiding device, can be deflected in such a way that the work channel is oriented laterally and in the direction towards the viewing direction of the optical unit.

According to a further preferred embodiment, which may be claimed independently, the work channel can be driven in a pushing manner from the proximal direction in order to effect the extension movement. In such a embodiment, the work channel has to have sufficient shear stiffness and has to be arranged on or in the endoscope shaft in such a way that it is relatively displaceable over its entire length. The advance can be effected manually or in a power-operated manner, e.g. by means of the hydraulics of an electric motor or the like.

According to a further, preferred embodiment, which may be claimed independently, the work channel can be arranged outside the endoscope shaft. For this purpose, for example, a tab can be formed in a sheathing of the endoscope, similar to a curtain, or an (elastically) stretchable double can be formed in the endoscope sheathing through which the work channel is guided along the endoscope shaft to the tip of the endoscope. Other, separate coupling elements can also be provided, e.g. a guide channel for the extendable work channel can be fixed with tape at regular intervals along the shaft.

According to a further, preferred embodiment, which may be claimed independently, the work channel can have its own (internal) actively bendable portion. For example, a Bowden cable can run in the wall of the extendable work channel so that it can be bent in a defined way from the handle portion in the extended state, e.g. to intubate the major duodenal papilla in a targeted manner. In such a embodiment, the work channel could be designed to move autonomously forward and backward and to bend from the endoscope.

According to a further, preferred embodiment, which may be claimed independently, the guiding device can have a portion made of a shape-memory material (wire) arranged at the distal end portion of the work channel, by means of which a defined curvature can be achieved in the second, extended position of the work channel.

According to a further, preferred embodiment, which may be claimed independently, the wall of the distal work channel portion can be constructed in a reinforced manner in order to better withstand the forces that occur when minimally invasive surgical instruments are pushed through. For this purpose, sleeves made of a rigid material or a wire mesh can be incorporated into the distal section of the work channel.

A further aspect, which may be claimed independently, relates to an endoscope or an adaptive endoscope head with a work channel arrangement, as described above. In order to make optimal use of the deflectability of the work channel and in order to be able to perform minimally invasive surgical treatments in both the orthograde and in the lateral direction, it is practical to provide imaging possibilities in both these directions. According to a embodiment, the endoscope or the endoscope head can have an optical unit looking in the axial direction and an additional optical unit looking in the lateral direction, or the optical unit can be converted from an orientation looking in the axial direction into a lateral one.

A further, independent aspect of the invention relates to an endoscope comprising at least one optical unit for image transmission; a lighting means or light guide and an individual work channel for guiding medical tools and/or for the flow of media. At least a (distal) portion of the work channel is designed to be flexurally elastic and extendable relative to the endoscope (in the axial direction). Due to the extendability in combination with the flexural elasticity, the work channel (portion) can be shifted from a first position, in which the work channel exit is oriented in the axial direction of the endoscope head, to a second position, extended distally with respect to the first position, in which the work channel exit is deflected/oriented in a predetermined lateral and/or retrospective direction by means of a guiding device.

A further, independent aspect of the invention relates to an endoscope head of the endoscope-adaptive type in the form of a separate, additional endoscope head attachment having an attachment means for detachable attachment to the endoscope head of an endoscope. The adaptive endoscope head according to the invention has at least one individual (separate) optical unit for image transmission; an individual (separate) lighting means or an individual (separate) light guide; and an individual work channel for guiding medical tools and/or for the flow of media. The work channel is designed to be flexurally elastic at least in sections and extendable relative to the endoscope head and can be shifted/transferred from a first position in which the work channel exit is oriented in the axial direction of the endoscope head to a second position extended distally relative to the first position. In the extended position, according to the invention the work channel exit can be deflected/oriented in a lateral or retrospective direction by means of a guiding device.

BRIEF DESCRIPTION OF THE FIGURES

FIG. 4 shows a perspective view of an endoscope according to a second embodiment of the invention with orthograde oriented work channel exit;

FIG. 5 shows a perspective view of an endoscope according to the second embodiment of the invention with extended, laterally oriented work channel exit;

FIG. 5A shows an alternative guiding device for an extendable work channel;

Figure 1:
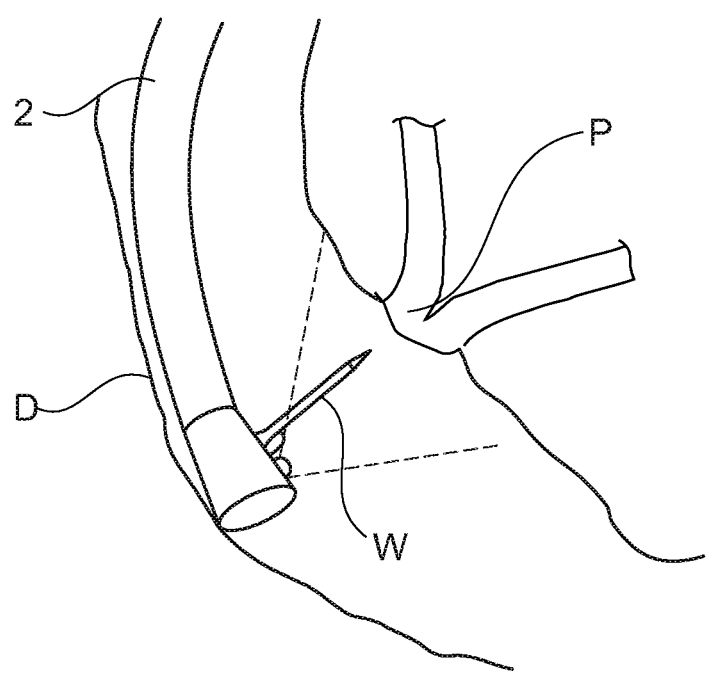
FIG. 1 shows a view for illustrating a field of application of an endoscope with a work channel arrangement according to the invention.

As can be seen from FIG. 1, the major duodenal papilla (P) is located in the rearward (dorsal) descending part (pars descendens) of the duodenum (D) and relatively difficult to access due to the tortuous geometry of this system. The space available in the region of the duodenum (D) is very limited, which means that procedures on the major duodenal papilla (P) are not possible with common prograde endoscopes, since at an appropriate angle, the endoscope tip would no longer have sufficient distance to the lumen of the duodenum (D) for proper imaging in the direction of the procedure portion.

Due to this reason, the aforementioned duodenoscopes are known from the prior art, which have a fixed sideways or retrospective optical unit as well as a correspondingly oriented working channel in order to make optimum use of the available space. However, such duodenoscopes have the disadvantage that they are fixed in their lateral/retrograde orientation of the optical unit and the working channel. On the one hand, this makes general navigation within the patient difficult and on the other hand makes such endoscopes inflexible in their possible applications. In other words, they are expensive special devices for a narrowly limited field of application.

A basic idea of the present invention is therefore to provide a work channel mechanism for an endoscope which is shiftable from an orientation looking straight ahead to a lateral or retrospective orientation.

FIRST EMBODIMENT

Figure 2:
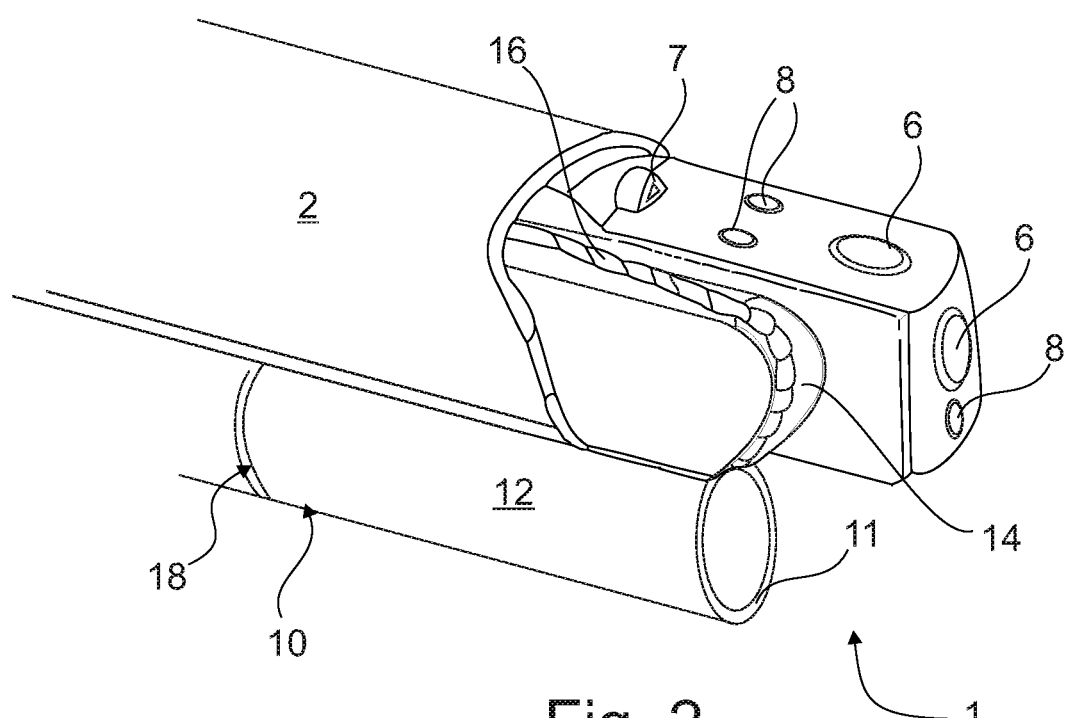
FIG. 2 shows a perspective view of an endoscope according to a first embodiment of the invention with orthograde oriented work channel exit.

FIG. 2 shows a first exemplary embodiment of an endoscope 2 according to the invention. An endoscope head 4 is arranged at the distal end of the endoscope 2, which has different functional units such as an optical unit 6; a cleaning nozzle 7 for the lens of the optical unit 6, and a lighting means 8. For the sake of clarity, only the most necessary functional units mentioned above are shown in the Figures; of course, an endoscope head 4 according to the invention can also have various other functional units known from the prior art, such as e.g. suction channels.

A work channel 10 of the endoscope 2 extends from its distal opening or its work channel exit 11 at the distal end of the endoscope 2, through a flexible shaft or along a flexible shaft of an endoscope 2 equipped with the endoscope head 4, to a proximal opening in the area of the endoscope handle (not shown) and can thus be used, for example, for the introduction of surgical instruments or tools (W), such as a papillotome, or for the application of media in the patient. The shown endoscope 2 furthermore has functional and supply channels running inside it (not shown), such as electrical lines, for supplying the functional units, for transmitting data, and for controlling the movements of the endoscope, which can be connected in the proximal direction to an operating station (not shown) or a controller/control device (also not shown). Furthermore, such an endoscope of the shaft type can have a so called deflecting portion between the endoscope head 4 and the preferably flexible endoscope shaft, which represents an actively-bendable shaft portion in extension of the passively-bendable endoscope shaft. This actively-bendable shaft portion can either be bendable in all directions or, if applicable, only in one direction, whereby in the latter case a rotation ring can be arranged between the deflecting portion and the endoscope shaft, which keeps the deflecting portion rotatable around the longitudinal axis of the endoscope with respect to the endoscope shaft.

Figure 3:
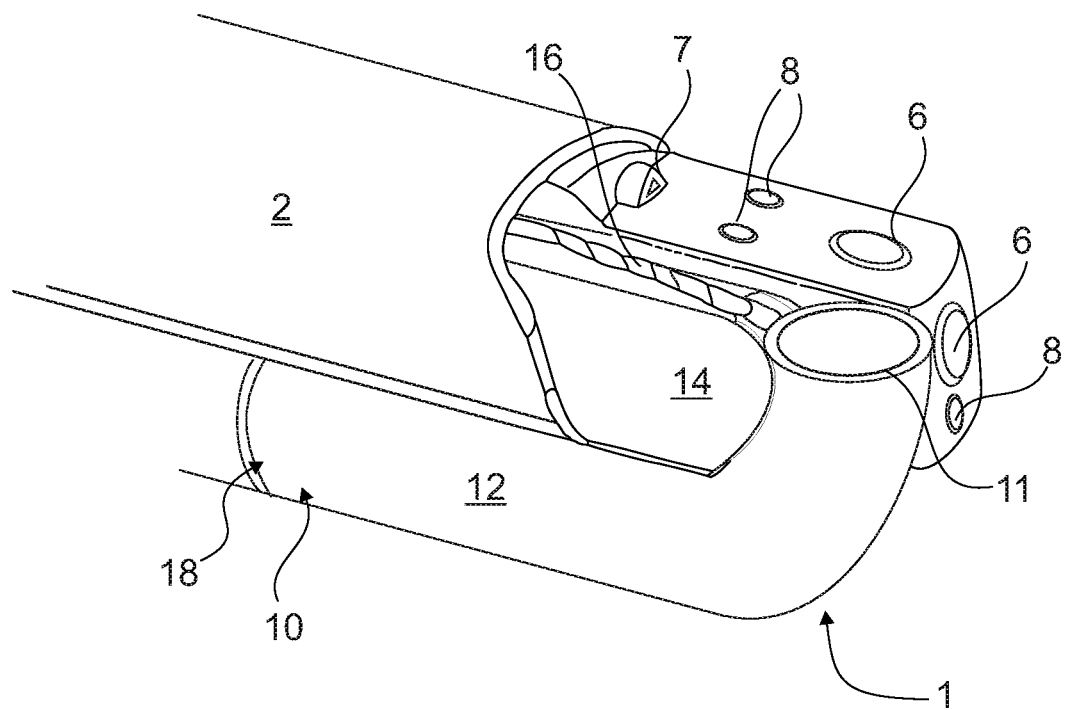
FIG. 3 shows a perspective view of an endoscope according to the first embodiment of the invention with an extended, laterally oriented work channel exit.

In the first embodiment of an endoscope according to the invention shown in FIGS. 2 and 3, the work channel 10 is held in an extendable manner. More precisely, a distal end portion 12 of the work channel 10 is telescopable relative to the work channel base body. However, the extendability can just as well be created in a different way, as is explained in more detail at another point. The distal end portion 12 of the work channel 10 is also kept flexurally elastic. The extendability of the work channel 10 in combination with the flexural elasticity ensures that the work channel 10 can be transferred from the proximally retracted position looking straight ahead as shown in FIG. 2 to the distally advanced and deflected position shown in FIG. 3.

In the first embodiment, the work channel is extended by an entrainer 16 (here a cable control). The entrainer can be actuated from the proximal handle piece and pulls the distal end portion 12 of the work channel 10 into the laterally oriented position. The telescopable distal end portion 12 of the work channel 10 extends from the work channel portion located proximally in front of it. During the extension movement, a guiding device 14 ensures that the work channel is deflected in a defined manner. In the first embodiment of the invention, the guiding device 14 is designed as a kind of ramp with a guiding groove or channel, which provides a defined curvature for the distal end portion 12 of the work channel 10. The guiding device 14 arches like a dome towards the distal endoscope end. In this way, the pulling force exerted by the entrainer 16 is deflected by the guiding device 14 by approximately 180° at the beginning of the pulling process, so that the work channel 10 is pulled distally forward, and acts proximally at the end of the pulling movement, so that the work channel 10 is held against the guiding device 14 and adapts to it. This ensures a defined radius of curvature through which a surgical instrument, for example, can be pushed and also prevents kinking when transferring the work channel 10 from orthograde to lateral orientation.

As can be seen in FIGS. 2 and 3, the work channel 10 basically runs on the side of the endoscope facing away from the optical unit 6. When the distal end portion 12 of the work channel 10 is extended and deflected, it is deflected by the guiding device 14 in such a way that it faces in the same direction as the optical unit 6. In this way, the radius of curvature of the work channel 10 is maximized in the deflected state, which facilitates the performance of minimally invasive surgical procedures. In this configuration version, the work channel 10 runs outside the endoscope shaft, but can also be located inside it (in the peripheral region), as can be seen in some of the following embodiments.

The entrainer 16 or the cable control of the first embodiment can be operated manually, e.g. by means of a rotary or toggle lever, or can be power-operated by means of an electric motor or a hydraulic system.

When the endoscope head 4 shown in FIGS. 2 and 3 is completely assembled, a cap is placed over it, which is not shown here, which shields the components and gives the endoscope head 4 a continuous, smooth contour at its distal end, which facilitates the insertion of the endoscope 2. Furthermore, the endoscope 2 of the first and all further embodiments can be covered with a protective cover in order to seal the endoscope 2 and to improve its sliding properties.

SECOND EMBODIMENT

In the second embodiment shown in FIGS. 4 and 5, the entire work channel 10 is designed to be movable relative to the endoscope in its axial direction. In this way, an advancing movement can be generated proximally from the handle part, which causes the distal work channel end to be extended. The advancing movement can, for example, be actuated manually via a rotary or lever mechanism or by means of a drive unit (e.g. linear motor). In such a embodiment, the work channel 10 has to be designed with a correspondingly high shear stiffness so that the advance movement can be transferred all the way to the distal tip of the endoscope. In the second embodiment of FIGS. 4 and 5, the guiding device 20 is designed as a kind of corset made of a shape memory material. In the advanced state, a predetermined, curved state of the guiding device 20 can be achieved by influencing the temperature from the handle part. For this purpose, the guiding device 20 is connected in a heat-conducting manner to a corresponding temperature influencing device (not shown). The corset-like guiding device also stiffens the distal end portion 12 of the work channel 10 so that it can force a deflection of minimally invasive surgical instruments and tools pushed through it.

In the second embodiment, the work channel 10 runs inside the endoscope shaft on the side of the endoscope 2 facing away from the optical unit 6 and is deflected by the guiding device 20 towards the viewing direction of the optical unit 6 to allow treatment in a lateral direction.

As an alternative or in addition to the shape-memory material, as shown in FIG. 5A, at least one separate Bowden cable 21 can be used as a guiding device for active angulation of the work channel 10. Here, the Bowden cable 21 runs largely in the wall of the work channel 10, exits the wall in an area in front of the work channel exit 11 and is anchored to the work channel 10 in the area of the work channel exit 11. In this way, the distal end portion 12 of the work channel 10 can be controlled (angled) autonomously from the handle part, e.g. by means of a lever or an electric drive, in order to intubate the major duodenal papilla in a targeted manner.

THIRD EMBODIMENT

Figure 6:
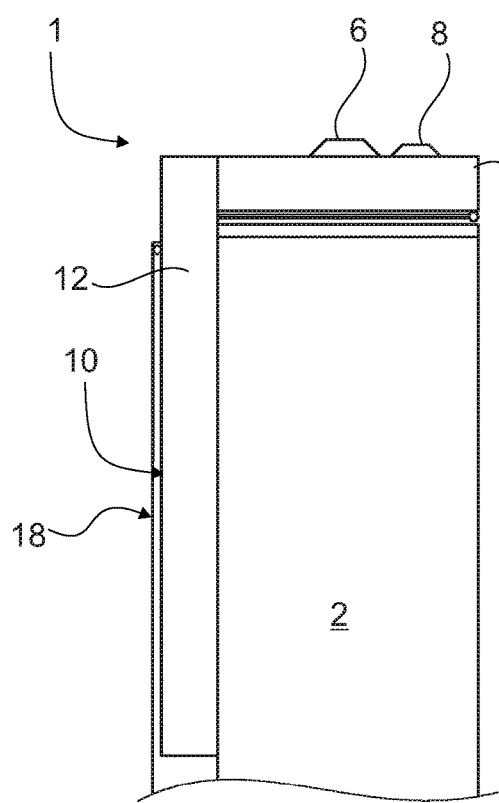
FIG. 6 shows a perspective view of an endoscope according to a third embodiment of the invention with orthograde oriented work channel exit.
Figure 7:
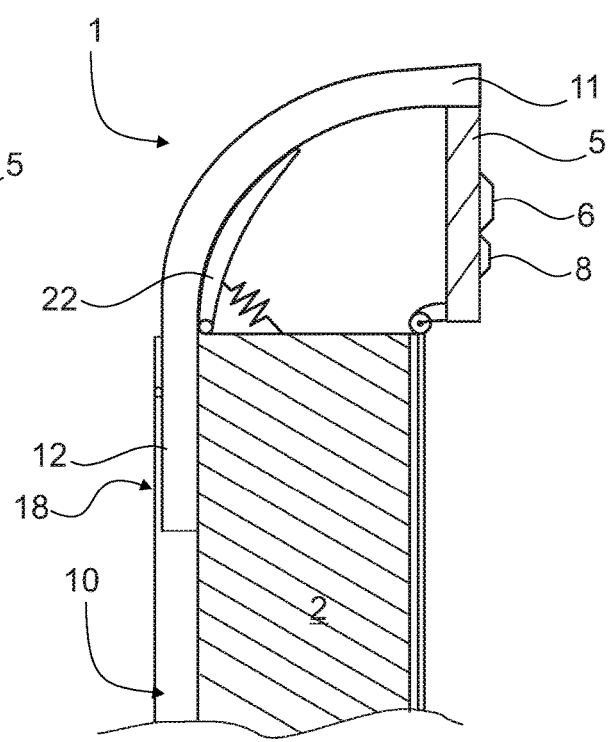
FIG. 7 shows a perspective view of an endoscope according to the third embodiment of the invention with extended, laterally oriented work channel exit.

In a third embodiment shown in FIGS. 6 and 7, a distal portion of the endoscope head 4 is configured as a pivotable end cap. In the example shown, the pivotable end cap is attached in an articulated manner to a hinge in the edge area of the endoscope head 4 and can be operated for pivoting, e.g. via a Bowden cable. The distal end portion 12 of the work channel 10 is anchored to the pivotable end portion of the endoscope head and is entrained when the head is pivoted.

In order to be able to operate in both the orthograde and the lateral direction with an endoscope according to the invention, it is important to have imaging capabilities in both of these directions. In the first embodiment shown in FIGS. 2 and 3, an optical unit 6 and lighting means 7 are each configured in duplicate, oriented once in the orthograde direction and once in the lateral direction. The user can thus switch back and forth between these two imaging modes or have both output simultaneously (e.g. on different screens), as required.

Figure 8:
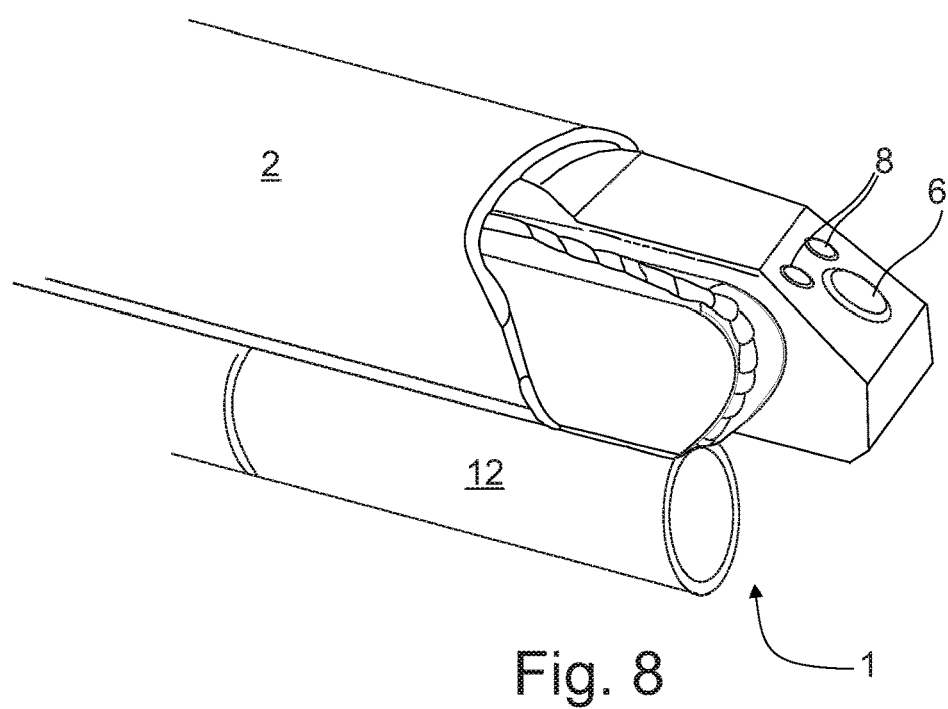
FIG. 8 shows a further embodiment with inclined optical unit.

A variant of an advantageous imaging device shown in FIG. 8 uses a single, obliquely (between orthograde and lateral) oriented optical unit 6. By using an optical unit 6 with a sufficiently wide angle of view, (surgical) work can be performed in both orthograde and lateral positions of the work channel 10. Preferably, the optical unit of an endoscope according to the invention can provide a viewing angle between 115° and 140°.

Figure 9:
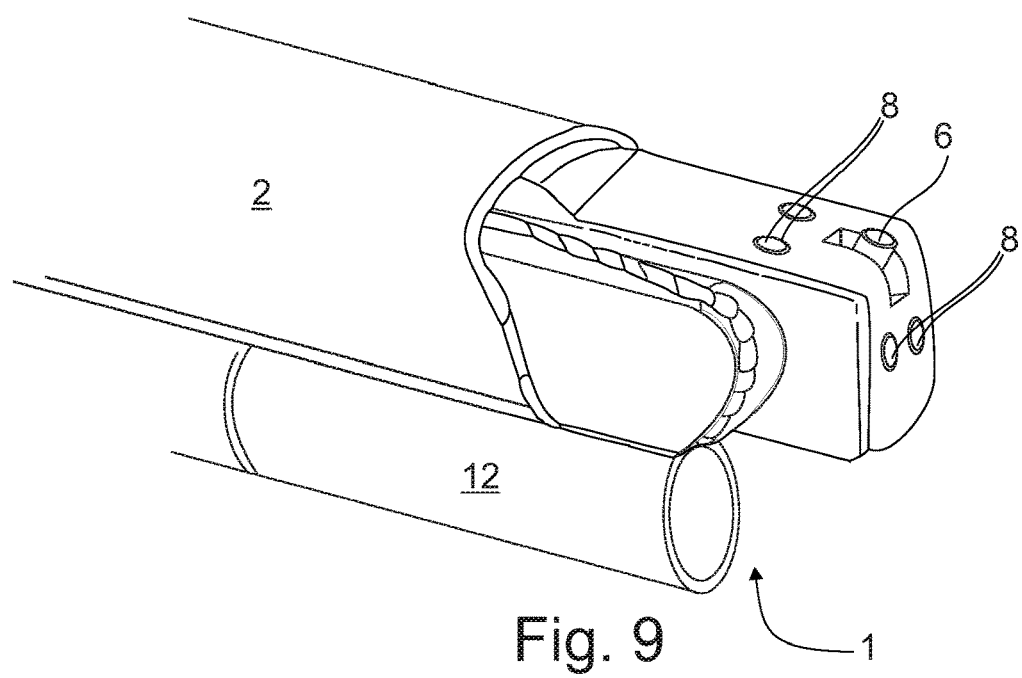
FIG. 9 shows a further embodiment with pivotable optical unit.

In a further configuration version, shown in FIG. 9, the optical unit 6 is designed to be pivotable. Comparable to a telescope in an observatory, the objective lens can protrude slightly from the surface of the endoscope head 4 and can be designed to pivot between an orthograde and a lateral orientation. A Bowden cable, a chain drive or the like can be used to pivot the optical unit. If the viewing angle is large enough, it is also sufficient if the optical unit 6 can pivot in an area between these two end positions.

As already indicated, there are several ways to achieve the extendability of the work channel. A telescope-like portion has already been described, which is shown in FIG. 6, for example. The telescope-like extension portion 18 has two or more cylindrical partial tubes with one lying coaxially inside the other. The distal, inner partial tube (here the distal end portion 12 of the work channel 10) can move out of the outer partial tube. Advantageously, a stop is provided which limits the extension movement (this can also be achieved by a slight conicity). In addition, a seal is provided between the relatively movable partial tubes in the embodiment shown.

Figure 10:
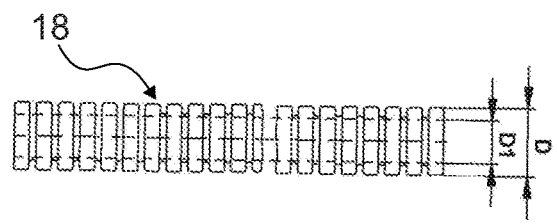
FIG. 10 shows an alternative extension portion for an extendable work channel.

FIG. 10 shows an alternative extension portion 18 of the corrugated tube design. The outer sheath of the work channel 10 is corrugated/gathered in such a embodiment. In the case of a tensile load, the tube/channel length required for the extension movement of the distal end portion of the work channel 12 can be obtained from this corrugated/gathered area.

The present embodiments can also be carried out without extension portion 18 by taking the work channel length required for the extension movement from its inherent elasticity, for example.

In the context of this disclosure, it is planned to combine elements of the embodiments described above. For example, an entrainer 16 according to the first embodiment could be combined with a shape-memory material portion 20 according to the second embodiment. Furthermore, the method of lengthening (telescope portion, corrugated tube, completely movable work channel, etc.) is interchangeable between the embodiments.

LIST OF REFERENCE SIGNS 1 work channel arrangement;
2 endoscope;
4 endoscope head;
5 distal end portion/end cap
6 optical unit;
7 cleaning nozzle;
8 lighting means;
10 work channel;
11 work channel exit;
12 distal end portion of the work channel;
14 guiding device/ramp;
16 entrainer;
18 extension portion/telescope portion;
20 guiding device/shape-memory material;
22 guiding device;
D duodenum;
P major duodenal papilla; and
W tool.

The invention claimed is:

1. An endoscope with an endoscope body, endoscope head extending in an axial direction, and a work channel arrangement for guiding medical tools and/or for the flow of media up to a distal endoscope head, the work channel arrangement comprising:

a work channel configured to be flexurally elastic at least in sections and extendable relative to the endoscope body, the work channel being movable between a first position, in which a work channel exit at a distal end of the work channel is oriented in the axial direction of the endoscope head, and a second position extended distally relative to the first position;

a guiding device configured to deflect the work channel exit in a predetermined lateral or retrospective direction relative to a longitudinal axis of the endoscope, when the work channel is in the second position; and a deflection device comprising an entrainer which is anchored at the work channel in an area of the work channel exit and operable from a handle part of the endoscope, the entrainer being configured to pull the work channel from the first position to the second position, the entrainer being positioned distally in front of the distal end of the work channel when the work channel is in the first position, and, being configured to, upon applying a tensile force to the entrainer from the proximal direction, first pull the work channel distally relative to the endoscope body and then pull the work channel into the predetermined lateral or retrospective direction relative to the longitudinal axis of the endoscope, when the work channel is in the second position.

2. The endoscope according to claim 1, wherein the guiding device comprises a guide surface which is convex towards the distal end of the endoscope, the guide surface being configured such that the work channel is pulled against the guide surface by the entrainer when the work channel is in the second position, whereby the guiding device supports the work channel from radially inside and gives the work channel a defined curvature due to the work channel's flexural elasticity.

3. The endoscope according to claim 2, wherein the guide surface is a convexly extending guide groove.

4. The endoscope according to claim 1, wherein the work channel has an extension portion that is configured to lengthen in the axial direction of the work channel when the work channel is subjected to a tensile load and thereby supports the extension movement of a distal work channel portion.

5. The endoscope according to claim 4, wherein the extension portion is a telescopable and/or expandable portion of the work channel.

6. The endoscope according to claim 1, wherein the endoscope comprises an optical unit facing in the axial direction and an additional optical unit facing in the lateral direction, or has an obliquely oriented optical unit, or the optical unit is configured so that it can be transferred from an orientation facing in the axial direction to an orientation facing in the lateral direction.

7. The endoscope according to claim 1, wherein the endoscope head is a separate, additional endoscope head attachment and comprises the work channel arrangement.

8. The endoscope according to claim 1, wherein the deflection device further includes the guiding device and the entrainer is deflected via the guiding device at a position distally in front of the distal end of the work channel when the work channel is in the first position.

* * * * *